United States Patent [19]

Thompson

[11] Patent Number: 4,788,969

[45] Date of Patent: Dec. 6, 1988

[54] STATIONARY SEAT CRUTCH

[76] Inventor: Marion E. Thompson, 2807 N. Prospect St., Colorado Springs, Colo. 80907

[21] Appl. No.: 876,934

[22] Filed: Jun. 20, 1986

[51] Int. Cl.[4] .................................................. A61F 5/02

[52] U.S. Cl. ......................................... 128/78; 128/68; 128/878; 297/413; 297/414; 297/415

[58] Field of Search ........................ 135/65, 67, 68, 69, 135/72, 74, DIG. 2, DIG. 9; 182/73, 150, 206; 248/105, 311, 340, 341, DIG. 3; 211/17, 18, 118; 297/56, 217, 253-256, 412, 413, 414, 415, 416; 272/67, 68, 63, 70.4; 128/78, 94

[56] References Cited

U.S. PATENT DOCUMENTS

| | | | |
|---|---|---|---|
| 766,484 | 8/1904 | Armstrong | 297/415 |
| 1,873,414 | 8/1932 | Jarvis | 297/413 |
| 1,984,855 | 12/1934 | Zwierzina | 297/413 |
| 2,584,732 | 2/1952 | Okun | 297/415 |
| 2,602,488 | 7/1952 | Conning | 297/415 |
| 2,637,372 | 5/1953 | Angelo | 297/254 |
| 2,650,650 | 9/1953 | Brown | 297/415 |
| 2,667,917 | 2/1954 | Dustin | 128/134 |
| 2,700,414 | 1/1955 | Bentley | 297/415 |
| 2,725,928 | 12/1955 | Branick | 297/415 |
| 2,805,704 | 9/1957 | Avseev | 297/255 |
| 3,169,036 | 2/1965 | Spooner | 297/156 |
| 3,391,891 | 7/1968 | Garden | 248/311.2 |
| 3,430,953 | 3/1969 | Teetor | 272/62 |
| 3,568,226 | 3/1971 | Mater et al. | 272/70.4 |
| 3,778,052 | 12/1973 | Andow et al. | 272/70.4 |
| 3,782,559 | 1/1974 | Wright | 211/17 |
| 3,874,657 | 4/1975 | Niebojewski | 272/63 |
| 3,881,644 | 5/1975 | Demaline | 224/153 |
| 4,108,170 | 8/1978 | Spann | 128/134 |
| 4,312,536 | 1/1982 | Lloyd | 297/217 |

FOREIGN PATENT DOCUMENTS

| | | | |
|---|---|---|---|
| 507690 | 11/1954 | Canada | 297/414 |
| 32420 | 7/1885 | Fed. Rep. of Germany | 297/415 |

*Primary Examiner*—Robert A. Hafer
*Assistant Examiner*—Charles H. Sam
*Attorney, Agent, or Firm*—Nixon & Vanderhye

[57] ABSTRACT

An adjustable seat crutch for relieving stress on the lower spine and buttock region during prolonged periods of sitting. The device includes at least one vertically and horizontally adjustable crutch support member for attachment to the upright back portion of a seat, and designed for engagement with one or both underarms of a user to support at least a portion of the upper body weight.

3 Claims, 1 Drawing Sheet

STATIONARY SEAT CRUTCH

BACKGROUND AND SUMMARY OF THE INVENTION

This invention relates to a therapeutic device for relieving stress on the lower spine and buttocks which often causes lower back pain when in a sitting position over a prolonged period of time.

It has long been recognized that one of the causes of lower back pain is the compression and/or pinching of nerves in the lower spine. Sitting over prolonged periods of time, even when sitting in a position in accord with good posture habits, can nevertheless result in such compression, causing discomfort and pain in the lower back and extending into the buttocks region. It is this condition which the present invention is intended to alleviate.

According to the present invention, an adjustable seat crutch is provided which is designed to be attached to the upright back portion of a seat. The seat crutch includes at least one padded support member which, in the operative position, extends outwardly from the seat back and which can be adjusted vertically to engage the arm or underarm of a user in a position such that at least a portion of the upper body weight of the user is supported by the crutch so as to relieve stresses on the lower spine and buttocks region. The seat crutch may include one supporting member if it is desired to support only one side of the upper body, or alternatively, the seat crutch may include a pair of support members for engagement with both arms of the user. In all cases the support members are adjustable both vertically and horizontally to accommodate users of varying physical characteristics. Several exemplary embodiments of the invention are disclosed. In one embodiment, there is provided a crutch component which includes a hook portion adapted to be hung over the seat back and an elongated flexible strap member which is designed to hang downwardly along the front face of the seat back. A padded support member is slideably mounted on the flexible strap member with fastening elements so that the padded support member can be adjusted vertically along the length of the strap as desired by the user. It is understood, of course, that the seat crutch may include two separate crutch components useable together to engage both arms or underarms of the user to provide substantially uniform relief of stresses on the lower spine and buttocks region.

In another similar embodiment, the padded support member may be slideably received on a depending flexible member through a threadable loop-type configuration explained more fully herein.

In a third embodiment of the invention, a pair of elongated crutch component members are provided in a scissors-type arrangement wherein the members are pivotally attached at a point intermediate their ends. The elongated members are provided with seat attaching hook means at their upper ends, and padded support members at their lower ends. The padded support members are mounted to the elongated members for adjustment to fit the requirements of the user.

In a fourth embodiment, the seat crutch consists of a single elongated member provided at its upper end with a curved hook-like portion for attachment to a seat back, and a single elongated transverse member adjustably mounted to the first elongated member. The transverse member is provided at either end with a padded support member. Each padded support member is adjustably mounted to the transversely extending member for adaptation to the size of the user.

In summary, it is the primary object of this invention to relieve stresses on the lower spine and buttocks region caused by upper body weight exerted on the lower spine when sitting for prolonged periods of time. To this end, an adjustable seat crutch is provided which engages the arms or underarms of a user and which supports at least a portion of the upper body weight.

DETAILED DESCRIPTION OF THE DRAWINGS

Figure 1:
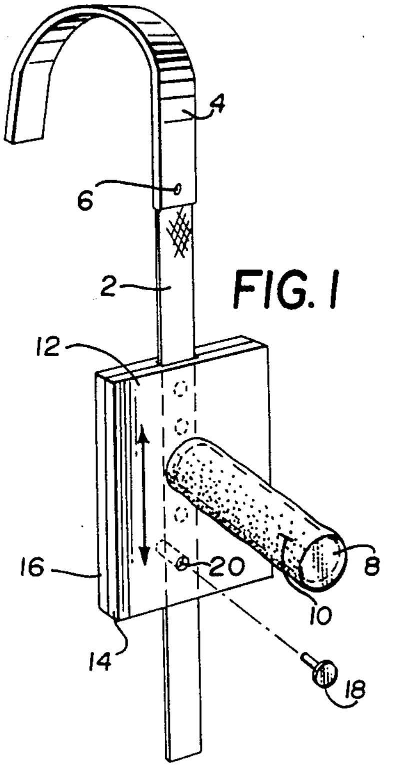
FIG. 1 is a perspective view of an adjustable seat crutch in accordance with an exemplary embodiment of this invention.

FIG. 1 illustrates a single adjustable seat crutch component which includes an elongated flexible member 2, which may be a strap of nylon mesh material for example, connected at one end to a hook-like member 4 by any conventional means such as rivet 6. The hook-like member 4 may be constructed of any suitable material such as aluminum, plastic, etc. A support member 8, constructed from rigid plastic or metal, is provided with padding 10 which may be in the form of a foam rubber sleeve, and is fixed at one end to a base element 12 slideably mounted on the elongated flexible member 2. Base member 12 is split into front and back elements 14, 16 respectively, which are releasably held together by any conventional fastening means such as screw 18 threadably received within a bore 20 extending between the two elements. Loosening the screw permits the base element along with the padded support member to be adjusted along the length of the elongated flexible member to a position where it engages the arm or underarm of the user. In this way the support member is not only adjustable to users of varying physical characteristics, but it is also adjustable to vary the degree of support provided by the crutch.

Figure 2:
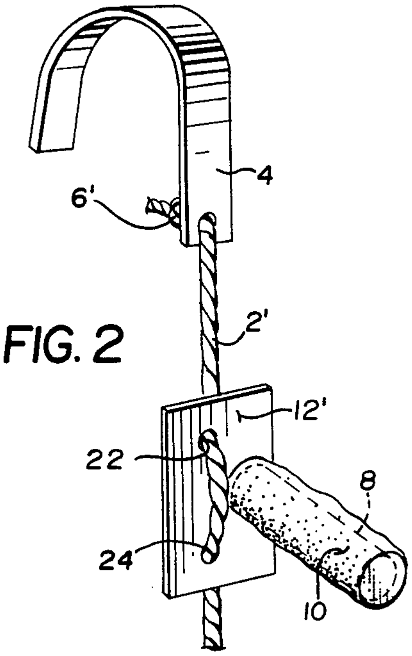
FIG. 2 is a perspective view of an alternative exemplary embodiment of the invention.

With reference to the embodiment shown in FIG. 2, an elongated flexible member 2' is attached to a hook-like member 4 by a knot 6' or other suitable fastening means. The elongated flexible member 2' in this case is in the form of a rope, for example such as nylon, and the base element 12' has formed therein a pair of apertures 22, 24 through which the elongated flexible member 2' is looped or threaded. As in the embodiment shown in Figure 1, the base element 12' along with the support member 8 may be adjusted along the length of the rope to the desired position. It is to be understood that one or more of the apertures 22, 24 may be provided with friction elements or the like for retaining the base element 12' in an adjusted position.

It is to be further understood that the adjustable seat crutch devices illustrated in FIGS. 1 and 2 can be used either singly or in pairs. It is readily apparent that when a pair of the crutch components are used together, both horizontal and vertical adjustment can be effected, and that uniform support of at least a portion of the upper body weight is provided.

Figure 3:
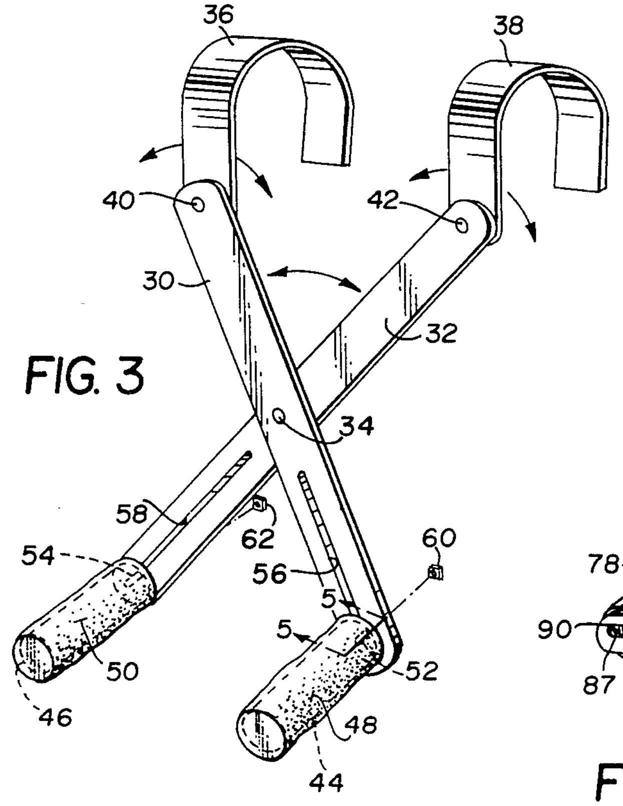
FIG. 3 is a perspective view of a third exemplary embodiment of the invention.
Figure 5:
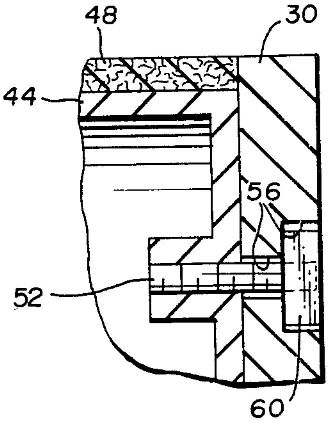
FIG. 5 is a plan view in cross section taken along the line 5—5 of FIG. 3.

In FIG. 3 there is illustrated an adjustable seat crutch, wherein two elongated relatively rigid members 30, 32 are fixed together intermediate their ends by a pivot connection 34. The members 30, 32 are provided at their upper ends with hook-like attachment members 36, 38 via loosely fitted rivet connections 40, 42, which permit members 36, 38 to rotate relative to members 30, 32. At their lower ends, members 30 and 32 are provided with support members 44, 46 on which are mounted suitable padding elements 48, 50. Support members 44, 46 are provided with threaded studs 52, 54 which extend through elongated slots 56, 58 formed in the elongated members 30, 32. Square nuts 60, 62 may be used to secure the support crutches in any desired position along the length of slots 56, 58. Details of the connection are shown in FIG. 5, where, for example, slot 56 is shown to be T-shaped to accommodate the nut 60. The slot configuration holds the nut 60 against rotation but allows it to slide axially along the slot and to fit flush with the member 30. It is to be noted further that because of the generally x-shaped or scissors-like configuration of the seat crutch in its operative position, movement of the support members within slots 56, 58 effect both horizontal and vertical adjustment. Because of the relatively loose connections at 40, 42, spreading of the support arms 44, 46 laterally does not alter the manner in which attachment members 36, 38 engage the seat back. Moreover, the scissors-like arrangement permits the device to be folded-up or collapsed when not in use.

Figure 4:
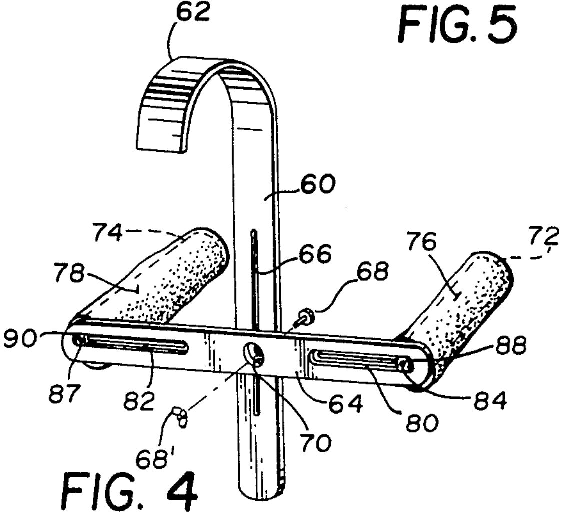
FIG. 4 is a perspective view of a fourth exemplary embodiment of the invention.

In FIG. 4, there is shown a still further embodiment of the invention wherein a single elongated relatively rigid member 60 is provided at its upper end with a hook-shaped portion 62 adapted to be hung over the top of a seat back. A second elongated member 64 is adjustably secured generally transverse to the first elongated member by means of a screw fastener 68 and nut 68' which extends through a recessed aperture 70 in member 64 and through an elongated slot 66 provided in the first elongated member 60. As is readily apparent, loosening of the screw fastener 68 permits vertical adjustment of the generally transverse second elongated member 64 up and down along the face of the seat back within limits defined by the slot 66. At either end of the transversely oriented member 64, there are provided support members 72, 74 provided with padding 76, 78. Support members 72, 74 are mounted for horizontal adjustment along recessed slots 80, 82 provided at either end of the elongated member 64. Again, suitable fastener means, such as screws and nuts, may be utilized to secure the support members in the desired position in the same manner, for example, as shown in FIG. 5. As with the embodiment illustrated in FIG. 3, the adjustable seat crutch disclosed in FIG. 4 is collapsible when not in use for ease in transport, storage, etc.

With respect to the exemplary embodiments of the invention shown in FIGS. 3 and 4, seat attachment members 36 and 38, as well as elongated members 30, 32, 60, 64 and crutch arms 44,46,72 and 74 may be made of any suitable lightweight material of sufficient strength, such as rigid plastics or metals including aluminum and steel.

Utilizing the apparatus heretofore described, it will be apparent that a method of relieving stress on the lower spine and buttocks of a human when in the sitting position is provided. The method comprises the steps of: providing at least one adjustable seat crutch component including attachment means adapted to be fitted over the substantially upright back portion of a seat, and at least one support member which in the operative position extends outwardly from the seat back in a direction substantially perpendicular thereto; adjusting the said at least one support member horizontally and vertically so as to engage at least one underarm of the user in a manner that provides support for at least a portion of the upper body weight; and optionally providing a pair of the said adjustable seat crutch components and adjusting the support member of each crutch component so as to engage both underarms of the user.

It will thus be seen that according to the present invention it is possible to provide relief of stress in the lower spine and buttocks area often encountered during prolonged periods of sitting. While the invention has been shown and described in what is presently conceived to be the most practical and preferred embodiments, it will be apparent to those of ordinary skill in the art that many modifications may be made thereof within the scope of the invention as particularly defined by the claims which follow.

What is claimed:

1. An adjustable seat crutch for relieving stress on the lower spine and buttocks of a user when in a sitting position on a seat having a generally upright back portion, said seat crutch including a pair of elongated seat crutch components pivotally interconnected intermediate their respective ends, said components comprising:

(a) attachment means for securing each of said seat crutch components to the generally upright back portion of the seat, said attachment means comprising a pair of curved hook-like members of generally inverted j-shape, each adapted to be hung over the generally upright back portion of the seat, and each secured to an upper end of a respective crutch component by means of a swivel joint;

(b) padded support means associated with said attachment means for engagement with at least one underarm of the user when in a sitting position to support at least a portion of the upper body weight wherein said padded support means comprises at least one elongated support member connected at one end to said adjustment means, said support member use extending outwardly from a front face of the generally upright back portion of the seat in a direction substantially perpendicular thereto; and (c) adjustment means mounting the padded support means to the elongated crutch component for vertical and horizontal adjustment relative to the generally upright back portion to accommodate users of varying physical characteristics and to adjust the degree of support provided by the crutch.

2. An adjustable seat crutch as defined in claim 1, wherein each of said pair of elongated crutch components are provided with said adjustment means, and wherein said adjustment means comprises a slot extending along a lower end of each of said components, an elongated support member being mounted for movement within each of said slots and wherein means are provided for securing each of said elongated support members within said slots.

3. A seat crutch comprising:

a pair of substantially identical and relatively rigid, curved hook-like members, each having a first free end, and a second end;

a pair of relatively rigid elongated members pivotally connected to each other at central portions thereof, and each of which is pivotally connected to, and extends from, said second end of each said hook-like member, said rigid elongated members each provided with an elongated slot;

a pair of support elements, one end of which extends outwardly from each said elongated member, generally perpendicularly thereto;

means for connecting said support elements to said elongated members so that said support elements are mounted for adjustable movement along the length of said elongated slots.

* * * * *